US00PP16231P3

(12) United States Plant Patent
Lintott

(10) Patent No.: US PP16,231 P3
(45) Date of Patent: Feb. 7, 2006

(54) ***CHRYSANTHEMUM* PLANT NAMED 'ALLEGRO JAZZ'**

(50) Latin Name: *Chrysanthemum morifolium*
Varietal Denomination: Allegro Jazz

(75) Inventor: Keith G. Lintott, Bognor Regis (GB)

(73) Assignee: Cleangro Ltd., Chichester (GB)

( * ) Notice: Subject to any disclaimer, the term of this patent is extended or adjusted under 35 U.S.C. 154(b) by 93 days.

(21) Appl. No.: 10/692,910

(22) Filed: Oct. 24, 2003

(65) Prior Publication Data

US 2004/0083516 P1 Apr. 29, 2004

Related U.S. Application Data

(60) Provisional application No. 60/421,392, filed on Oct. 25, 2002.

(51) Int. Cl.
*A01H 5/00* (2006.01)

(52) U.S. Cl. ..... Plt./292
(58) Field of Classification Search ..... Plt./292
See application file for complete search history.

(56) References Cited

U.S. PATENT DOCUMENTS

PP5,324 P 11/1984 Duffett ..... Plt./76

OTHER PUBLICATIONS

UPOV–ROM GTITM Computer Database 2003/06, GTI Jouve Retrieval Software, Citation for 'Allegro'.*

Royal Van Zanten Garden Mum Catalog 2002, listing *Chrysanthemum* variety 'Allegro' at pp. 6 (color picture), 9 and 14.

Royal Van Zanten/Van Zanten Cuttings B.V. 2003–2004 European Catalog, listing *Chrysanthemum* variety 'Endurance' at pp. 26–27.

*Chrysanthemum* Breeders Association Catalogue 2001, listing a variety 'Allegro' at p. 10.

*Chrysanthemum* Breeders Association Catalogue 2002, listing a variety 'Allegro' at p. 10.

*Chrysanthemum* Breeders Association Catalogue 2003, listing a variety 'Allegro' at p. 10.

* cited by examiner

*Primary Examiner*—Anne Marie Grunberg
*Assistant Examiner*—Annette H Para
(74) *Attorney, Agent, or Firm*—Winston & Strawn LLP

(57) ABSTRACT

A new variety of *Chrysanthemum* plant named 'Allegro Jazz' having a good uniform canopy of bright purple decorative flowers. The new variety has medium vigor, a free branching and uniform spreading habit, and good foliage presentation.

1 Drawing Sheet

Latin name of the genus and species: Botanical classification: *Chrysanthemum morifolium.*

Variety denomination: The new *Chrysanthemum* variety denomination is 'Allegro Jazz.'

BACKGROUND OF THE INVENTION

The present invention comprises a new and distinct cultivar of *Chrysanthemum* botanically known as *Chrysanthemum morifolium*, and referred to by the cultivar name 'Allegro Jazz.'

'Allegro Jazz,' identified as 31037, originated from a cross made in a controlled breeding program in Chichester, West Sussex, United Kingdom. The female parent of the new variety is the unpatented variety 'Endurance.' The male parent of the new variety is an undistributed, unpatented seedling identified as 'G5E6.' The new variety 'Allegro Jazz' has been asexually reproduced by vegetative cuttings in Chichester, West Sussex, United Kingdom and the distinguishing characteristics are retained through successive generations of asexual reproduction.

BRIEF SUMMARY OF THE INVENTION

'Allegro Jazz' is a garden type of *Chrysanthemum* plant having a domed-round plant form carrying bright purple decorative flowers.

Comparison with Female Parent

Plants of the new *Chrysanthemum* variety 'Allegro Jazz' are dissimilar to the parent 'Endurance' in plant habit and growth rate. In side-by-side comparisons in Chichester, West Sussex, United Kingdom, under commercial practice, plants of the new *Chrysanthemum* variety 'Allegro Jazz' differed from plants of the parent 'Endurance' in the following characteristics.

1. The new variety 'Allegro Jazz' produces light purple medium sized decorative flowers whereas the parent 'Endurance' produces deep purple small type decorative flowers.
2. Plants of the new variety 'Allegro Jazz' have larger and shorter inflorescence than plants of the parent 'Endurance.'
3. The variety 'Allegro Jazz' has a more round shape habit than the parent variety 'Endurance.'

Comparison with Other Varieties

Plants of the new *Chrysanthemum* variety 'Allegro Jazz' are similar to the patented variety 'Debonair' (U.S. Plant Pat. No. 5,324) in plant habit and growth rate. However, in side-by-side comparisons in Chichester, West Sussex, United Kingdom, under commercial practice, plants of the new *Chrysanthemum* variety 'Allegro Jazz' differed from plants of 'Debonair' in the following characteristics.

1. The new variety 'Allegro Jazz' produces a deeper purple colored flower than 'Debonair.'
2. The new variety 'Allegro Jazz' produces larger flowers than 'Debonair.'
3. The new variety 'Allegro Jazz' has a more round shape than 'Debonair.'

BRIEF DESCRIPTION OF ILLUSTRATION

Typical specimens of the plant and flowers for the new *Chrysanthemum* variety 'Allegro Jazz' are shown in the accompanying digital photograph. The colors shown are as true as possible within the usual limits of this kind of illustration.

FIG. 1 is a whole plant view of the new variety 'Allegro Jazz' grown in a pot. The plant shown in the illustration is 70 days from the commencement of planting outdoors in mid-June.

DETAILED BOTANICAL DESCRIPTION

The following description of the new *Chrysanthemum* variety 'Allegro Jazz' is of plants grown outside, natural season, in Chichester, West Sussex, United Kingdom in the month of June. The cultivar has not been observed under all possible environmental conditions. The phenotype may vary significantly with variations in the environment such as temperature, length of day and light intensity, without any variance in genotype. The commercial classification of the new variety is a garden *Chrysanthemum.*

Plants of the new variety have been grown successfully under temperature conditions averaging about 50° F. at night and about 60° F. to 75° F. during the day under natural light conditions. The plants were grown outdoors in mid-June in 4 liter pots using a loamless compost. No growth retardants were used. To produce a commercial product the plants may be pinched once with the center bud removed. The typical container size for commercial growth is 4 liters (8"). It has been observed that the shelf life of the new variety is about 26 days with a response time of about 10 weeks. The new variety is suitable for growth in a temperature range of 50° F. to 75° F.

The new variety may be produced as a pot plant. The following description is with respect to a plant produced as a garden pot plant. In the description of this new *Chrysanthemum* variety, color values have been taken from The Royal Horticultural Society Colour Chart (R.H.S.C.C.).

Plant

Plant type: Pot.
Habit: Domed—Round.
Height: 40 cm.
Width: 60 cm.
Branching characteristics: Upright and Free Branching.
Length of lateral branches: 15–30 cm.
Number of breaks from pinch: 7–9.
Stem color: Near 137A.
Response time: 70 days natural season.
Vigor: Medium.
Shelf life: 26 days.
Disease (susceptibility/resistance observed): None observed to date.
Pest (susceptibility/resistance observed): None observed to date.
Growth retardant type and treatment: No treatment necessary. The plants were grown for 10 weeks in natural season conditions.
Propagation:
*Type.*—Vegetative Propagation via Stem Cuttings.
*Time to rooting.*—12 days with soil temperatures of 70° F.
*Rooting habit.*—Fine and Fibrous.

Foliage

Number of leaves per lateral branch: 11–17.
Compound or single: Single.
Arrangement of leaves: Alternate.
*Shape of leaf.*—Typically 5 lobed ovate.
*Size of leaf.*—Width (cm): 2–4. Length (cm): 3–5.5.
*Leaf apex.*—Acute.
*Base.*—Truncate.
*Attachment.*—Petioled.
*Aspect.*—Slightly Undulating.
*Margin.*—Palmately Lobed.
*Surface characteristics.*—Top: Very Slightly Pubescent Bottom: Very Slightly Pubescent.
Petiole:
*Color.*—Near 138B.
*Length.*—1–1.5 cm.
*Diameter.*—0.2–0.3 cm.
Venation: Net prominent mid vein at underside.
*Color.*—Upper side: near 138B. Under side: near 138C.
Color:
*Mature leaf, upper side.*—Near 137C; under side: near 147C.
*Young leaf, upper side.*—Near 137B; under side: near 147C.

Flower

Flower appearance: Matte.
Flower type: Decorative.
Flower form: Domed.
Flower shape: Circular.
Flowering habit: Cyme.
Number of blossoms per branch: 11–15.
Inflorescence form: Corymibiform.
*Depth of fully expanded blossoms.*—1.5–2 cm.
*Diameter of fully expanded blossoms.*—2.5–4 cm.
Phyllaries:
*Number.*—32–35.
*Color.*—Near 136C.
*Length.*—4–6 mm.
*Width.*—1–1.5 mm.
*Texture/appearance.*—Very slightly pubescent.
Pedicel:
*Length: Terminal:* 4.5–6 cm; lateral: 7–11 cm.
*Color.*—Near 136C.
*Surface.*—Slightly pubescent.
*Habit.*—Slightly curving.
*Strength.*—Medium/Strong.
Peduncle:
*Length.*—Terminal: 5–6 cm; lateral: 7–8 cm.
*Diameter.*—0.3–0.5 cm.
*Color.*—Near 147A.
*Habit.*—Slightly curving.
*Surface.*—Slightly pubescent.
*Strength.*—Moderately strong.

Ray florets:
*Form/shape.*—Reflexing with oblong shape.
*Texture/appearance.*—Matte.
*Number per flower.*—240–260.
*Length.*—0.8–2 cm; Width: 2–7 mm.
*Apex.*—Rounded.
*Base.*—Tapered.
*Margin.*—Entire.
Disc florets:
*Form/shape.*—Cylindrical.
*Texture/appearance.*—Shiny.
*Number per flower.*—1–5.
*Length.*—5–6 mm; Width: <1 mm.
*Diameter of disc.*—<1 mm.
Fragrance: None.
Flower bud (at onset of color):
*Length.*—5–7 mm.
*Diameter.*—5–9 mm.
*Form/shape.*—Globular.
General flower color:
1. *Ray florets, upper side.*—Immature: near 64B. Mature: near 64C. Older/Fading: near 68C.
2. *Ray florets, under side.*—Immature: near 64B. Mature: near 64C. Older/Fading: near 68C.
3. *Disc florets.*—Immature: near 68D. Mature: near 68D. Older/Fading: near 68D.
4. *Bud.*—145C.

Flower progression with age: Color fades uniformly with age.

Reproductive Organs

Gynoecium present on ray and disc florets.
Ray florets per individual flower:
*Pistil number.*—100–125 observed.
*Stigma color.*—Near 144D.
*Stigma shape.*—Forked.
*Style color.*—Near 144D.
*Style length.*—3 mm.
Disc florets per individual flower:
*Pistil number.*—1–3.
*Stigma color.*—Near 144D.
*Stigma shape.*—Forked.
*Style color.*—Near 144D.
*Style length.*—4 mm.
Androecium present on disc florets only.
*Stamen number.*—About 5.
*Anther shape.*—Cylindrical.
*Anther color.*—Near 14C.
*Pollen color.*—Near 12A.
*Pollen quantity.*—Slight.
Fruit and seeds: None observed.

What is claimed is:

1. A new and distinct variety of *Chrysanthemum* plant, substantially as described and illustrated herein.

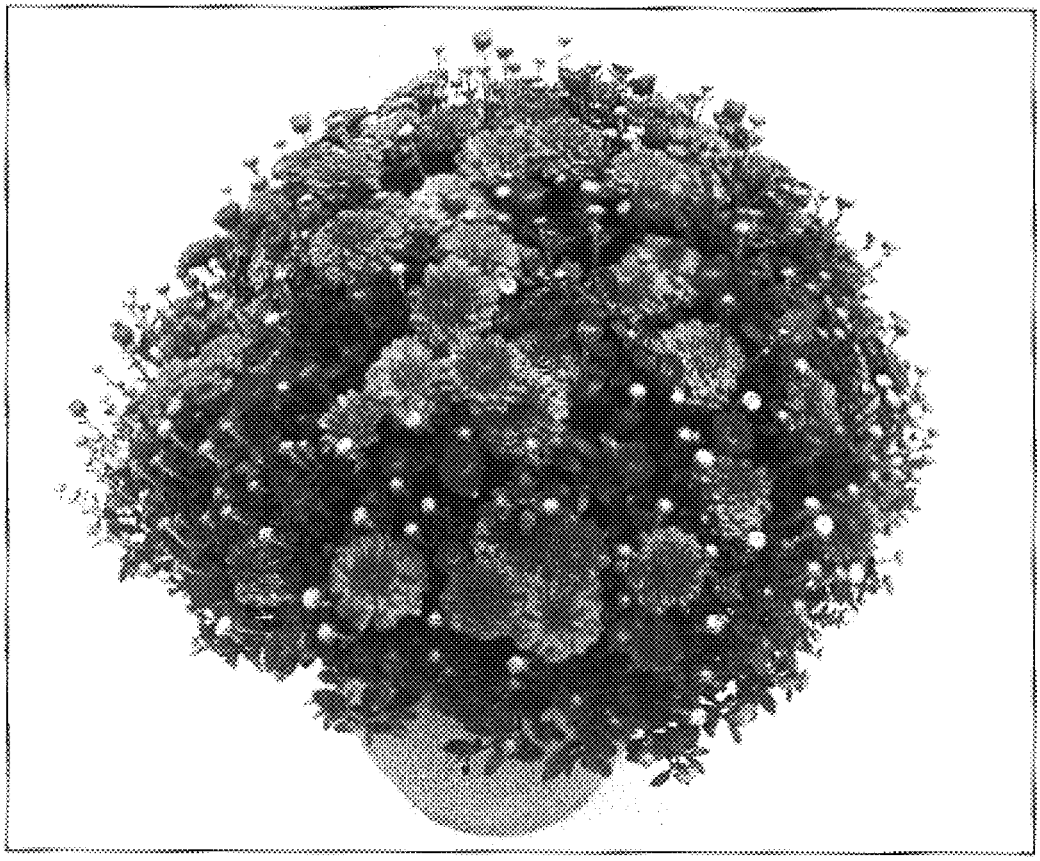

* * * * *